United States Patent [19]
Ellis

[11] Patent Number: 5,636,255
[45] Date of Patent: Jun. 3, 1997

[54] METHOD AND APPARATUS FOR CT IMAGE REGISTRATION

[75] Inventor: Randy E. Ellis, Kingston, Canada

[73] Assignee: Queen's University at Kingston, Kingston, Canada

[21] Appl. No.: 610,938

[22] Filed: Mar. 5, 1996

[51] Int. Cl.⁶ .................................................. A61B 19/00
[52] U.S. Cl. .................................................. 378/20; 606/130
[58] Field of Search ....................... 378/20; 364/413.13, 364/413.14; 606/130

[56] References Cited

U.S. PATENT DOCUMENTS 4,991,579  2/1991  Allen ........................................ 128/653
5,397,329  3/1995  Allen ........................................ 606/73

*Primary Examiner*—Michael J. Tokar
*Assistant Examiner*—David Vernon Bruce
*Attorney, Agent, or Firm*—Richard J. Hicks

[57] ABSTRACT

A method and system for correlating accuracy of computer tomography (CT) image resolution is described. Small radio-opaque markers having a diameter less than one slice width of a CT scan are embedded in the object, such as a bony skeletal member, to be measured, the object is then CT scanned so that the radio-opaque markers appear in at two slices of the scan. The markers are also physically located by detecting them with a sensor, such as a positioning pointer. Also described is one form of marker comprising a tantalum sphere mounted in a ceramic, preferably alumina, pin.

19 Claims, 2 Drawing Sheets

METHOD AND APPARATUS FOR CT IMAGE REGISTRATION

FIELD OF INVENTION

This invention relates to Computed Tomography (CT) scanning devices and methods for CT image registration. More particularly, this invention relates to methods and apparatus for accurately registering and correlating accuracy of 3D images, typically CT images with intra-operative data collected by other means such as a pointing device, in a clinical setting.

BACKGROUND OF INVENTION

There is rapidly growing interest in extending the capabilities of image guided machining and cutting techniques and to adapting such techniques to unconventional areas such as surgery. Computed-assisted and robotic-assisted machining, and in particular computer-assisted and robotic-assisted surgery, requires accurate registration of a 3D image, typically computed tomography (CT) images, to intra-operative data collected by a pointing or other detecting and locating device. An impediment to successful registration is that the accuracy achievable with laboratory phantoms cannot be transferred into a machine shop or clinical setting: the phantoms and the methods used to isolate their locations are incompatible with normal machine shop or surgical practise.

Some current computer-assisted orthopaedic systems and robotic neurosurgery systems use large invasive markers that are implanted pre-operatively, under anaesthetic, or attempt to identify natural landmarks. ACT scan is then taken, and the images are processed semi-automatically to estimate the marker or landmarks locations. In surgery, the markers or landmarks are touched by a 3-D sensing apparatus, and point to point registration is performed. The best registration these approaches can regularly provide is ±2 mm, which is generally considered too imprecise for such procedures as knee surgery where there is a need for registration to be within ±1 mm in position and ±1° in rotation. It has been found that misplacement of prosthetic knee components by only 2.5 mm can severely affect the range of flexion and other kinematic variables. Furthermore, the placement of the relatively large markers can often cause pain to the patient and it is unusual for such markers to be left in place permanently.

There is, therefore, a need for a less invasive, more accurate, registration technique for these surgical and other applications.

OBJECT OF INVENTION

It is, therefore, one object of the present invention to provide an improved registration method for use with CT scan data for use in surgical and other precision applications.

Another object of the invention is to provide a system for deriving high accuracy correlation between CT scan data and data derived from other sources.

Another object of the invention is to provide an improved marker device for use in the registration method for CT scan data.

BRIEF STATEMENT OF INVENTION

By one aspect of this invention there is provided a method for deriving high accuracy correlation between data obtained by a computer tomography (CT) scan, in which an object is scanned in a plurality of CT slices, and data relating to said object obtained from other sources, comprising:

providing in said object at least one radio-opaque marker having a diameter less than one slice width of said CT scan;

detecting said radio-opaque marker in at least two said slices; and determining a three dimensional position of said marker therefrom for comparison with said from other sources.

By another aspect of this invention there is provided a system for deriving high accuracy correlation between data obtained by a CT scan, and data obtained from other sources, comprising:

(a) means for CT scanning in a plurality of slices of selected bandwith;

(b) radio opaque marker means having a diameter of less than said selected bandwidth;

(c) means for detecting said radio opaque marker in at least two said slices; and (d) means for deriving said data obtained from other sources.

By another aspect of this invention there is provided a marker for use in computed tomography (CT) scanning, comprising:

a radio-opaque marker element;

a radio luscent holder adapted to receive said marker element; and means to secure said marker in said holder;

wherein said marker element has a diameter less than one CT scan slice width.

DETAILED DESCRIPTION OF PREFERRED EMBODIMENTS

Figure 1:
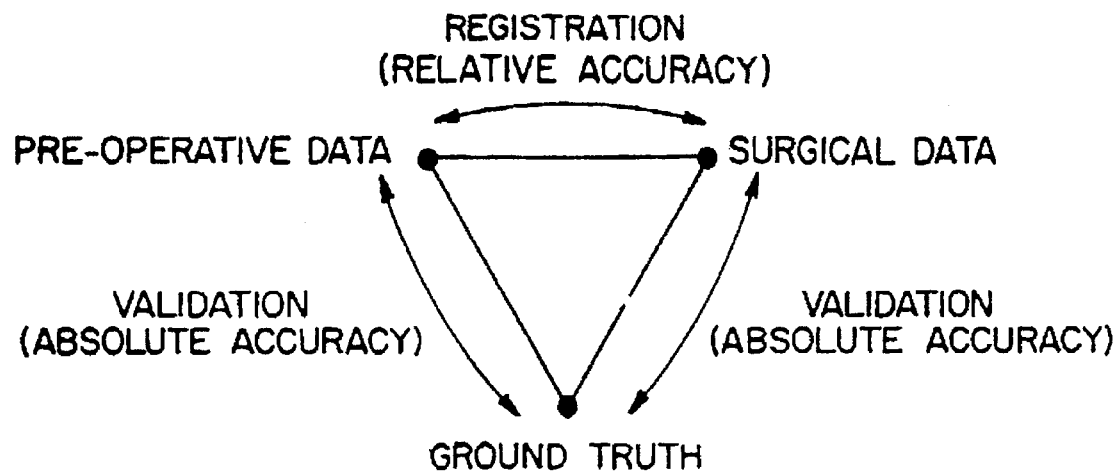
FIG. 1 is a sketch illustrating "the accuracy triangle for evaluating registration"

As a step towards an accurate and clinically applicable registration, the use of a fiducial marker that can be used as a "ground truth" for evaluating registrations has been examined. The error arising from a registration can be established if two sources of data can be correlated to ground truth; in image-guided surgery (for example), the data sources might be a pre-operative CT scan and intra-operative pointer locations. The accuracy triangle, shown in FIG. 1, expresses the errors between the measuring modalities and can be used to evaluate the effectiveness of a registration: if two measuring modalities are absolutely accurate (if they register to ground truth with low error) then their relative accuracy can also be trusted.

Accuracy evaluation thus depends on a ground truth. Roentgen Stereogrammetric Analysis (RSA) is one well established analytical technique for finding the 3D location of small markers, and it has been found that the markers appear dearly on CT images. Since the markers can also be located with a pointing device or other locating technique, the RSA data can act as the ground truth and the accuracy of the registration of CT images to pointer data can be evaluated. However, in order to correlate the CT images to the RSA data, the tiny RSA spheres must be accurately located in the CT scans.

One approach to detecting the small spheres is to utilize the beam spread of typical CT machines to advantage, and interpolate from multiple slices to find the CT locations of the RSA markers. Results indicate that it is possible to register the locations of fiducial in CT images to pointer locations with high certainty. An accurate fiducial registration can in turn be used to evaluate the accuracy of registration from anatomical or other landmarks, which is the ultimate goal of surgical registration.

In order to establish that RSA is a method for evaluating the registration of CT images to surgical data, requires a method for registering the locations of fiducial markers, as determined by one measuring system, to the locations of the same markers determined by some other measuring system. The registration method chosen is one that minimizes the least-squares error between the data in one set (call it the source) with data in another set (call it the reference). For n source data points, let pi be the $i^{th}$ data point of the source data set P and let $x_i$ be the corresponding data point of the reference set X. If the registration is a 3×3 rotation matrix R and a translation vector q, the objective function to be minimized is $$f(R, \vec{q}) = \frac{1}{n} \sum_{i=1}^{n} \|\vec{x_i} - R\vec{p_i} - \vec{q}\|^2 \quad (1)$$

where ‖•‖ is the usual Euclidean norm. The correspondence between source data and reference data, and the optimal registration, can be found simultaneously using the iterative closest-point (ICP) algorithm of Besl and McKay.

Figure 4:
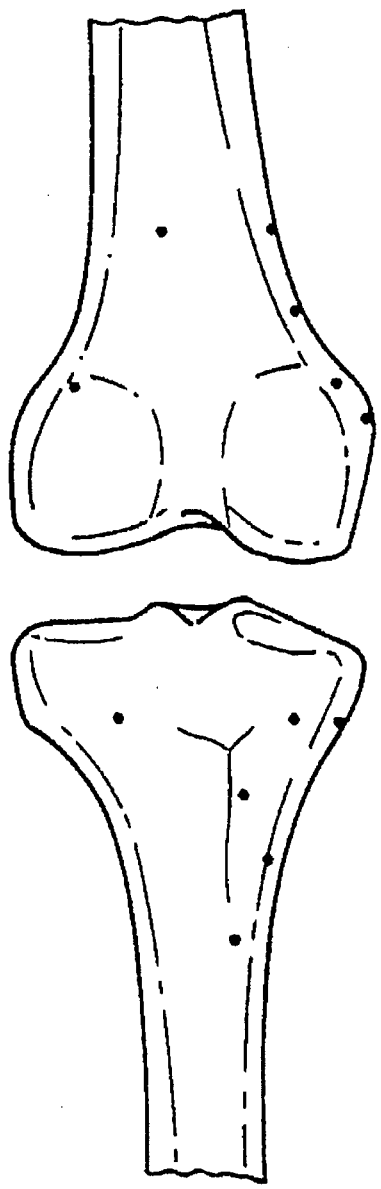
FIG. 4 is a sketch illustrating locations of RSA markers in a knee joint.

Laboratory phantoms were used to assess the use of RSA markers as fiducials in assessing the accuracy of CT registrations. The phantoms were selected with computer-assisted surgery in mind. Phantom number 1 was a plastic model of human femur (Pacific Research Laboratories model 1103), and phantom number 2 was a plastic model of a tibia (Pacific Research Laboratories model 1101). Each bone was instrumented with 6 tantalum spheres, 0.80 mm in diameter, the locations selected to be external to the joint capsule but within the normal operating field of total knee replacement surgery. Holes of diameter 0.7 mm were drilled, and the spheres were pressed with an interference fit so that they slightly protruded from the bone surface; the spheres were then secured with a thin covering of cyanoacrylate adhesive. FIG. 4, indicates the locations of the markers. The 3D location of each marker was measured in three ways: with RSA, with CT scans, and with direct contact by a 3D measuring device.

Roentgen stereogrammetic analysis is a radio-graphic technique for locating small spherical markers in three dimensions. The object under study is imaged within (or near) a precision calibration structure; the geometry of the X-ray sources and films is deduced from the calibration cage, and the locations of the centers of the markers is then estimated. The markers are usually made of tantalum, which is highly radio-opaque and yet is sufficiently biocompatible to withstand long-term implantation in human patients.

Accuracy and repeatability of 10 micrometers or less is not uncommon in a laboratory setting, and less than 200 micrometers is easily achieved in a clinical setting (motion of the patient affects the accuracy). The method has been studied for accuracy and has extensively been used for studying the three-dimensional micromotion kinematics of: hip prostheses; knee prostheses; femoral fractures; ligament grafts; and lumbar orthoses.

It was possible to interpret CT images of the markers in two ways: the surfaces of the small spherical markers could be deduced, or the centers could be deduced. Because of the high absorption coefficient of tantalum, there are some reconstruction artifacts in the CT images that present severe difficulties in deducting small surfaces accurately. Thus, for the purposes of this work, the CT data are the interpolated centers of the markers and the RSA data are also marker centers.

A single CT slice is a reconstruction of a sequence of X-ray exposures. The geometry of each exposure can be used to advantage in achieving sub-voxel estimation of small objects in the CT tunnel.

Figure 2:
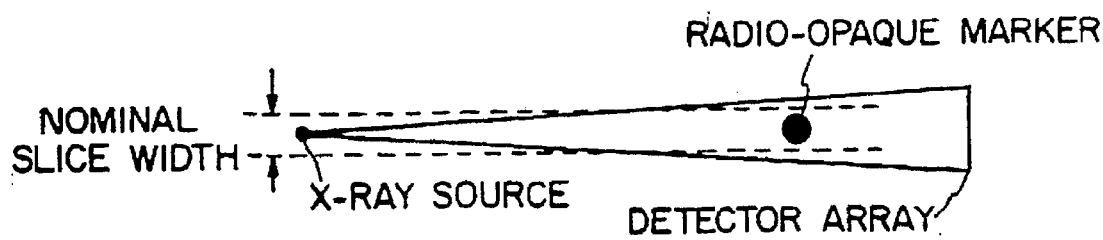
FIG. 2 is a sketch illustrating trans-slice geometry of a CT exposure of a small sphere.

FIG. 2 show the pertinent imaging geometry of a typical CT machine. (The figure displays the geometry not of an entire slice, but rather with the moving axis of the table as the vertical axis and thus with the slice perpendicular to the page). For each exposure, a collimator limits the angular dispersion of the beam; note that because the beam is a fan but the slice is a rectangle from this perspective, the slice width can mathematically be chosen so that part of the beam within the scanned field of view lies outside the nominal slice width. Suppose that the nominal slice width is 1.0 mm, and that a 0.8 mm sphere is present as illustrated.

Figure 3:
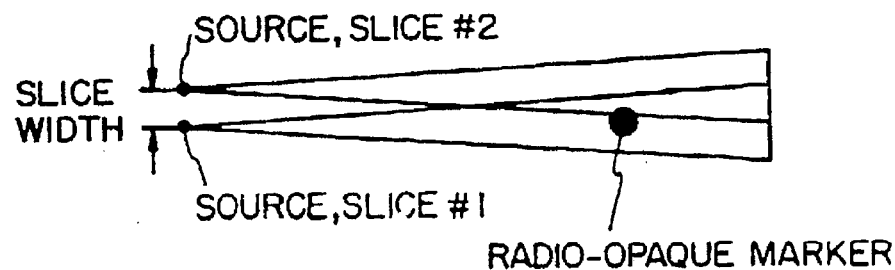
FIG. 3 is a sketch illustrating trans-slice geometry of multiple CT exposures of a small sphere.

In FIG. 3 the imaging is displayed showing an adjacent contiguous slice being taken. Because of the fan-shaped beam, although the 0.8 mm sphere is smaller than the nominal slice width it is in fact absorbing radiation and thus is detectable in the adjacent slice.

In the present studies the overlap effect was highly repeatable: out of a total of 36 images of tantalum spheres, every sphere appeared on at least two slices (and frequently appeared on three slices). This permitted use of an interpolation algorithm to be estimate the center of the sphere to sub-slice accuracy.

Experimental Procedure

The first measurement of the phantoms was with RSA, taking 1 radiographic set on one day (a pilot set) and 6 sets on another day (verification sets). All RSA films were processed by the same technician.

The second measurement was with CT, by taking images on a CT Sytec (GE Medical Systems, Milwaukee, Wis., USA); settings were 120 kV, 40 mA, bone reconstruction algorithm, 1 mm contiguous slices, 200 mm nominal field of view (which we corrected to 204.8 mm using a phantom). Two sets were taken 20 days apart but within the same maintenance period, and a subsequent image set was taken after periodic maintenance in order to verify repeatability.

Centers of the tantalum spheres were estimated using an automated center-of-gravity calculation from the reconstructed CT data. A threshold was selected based on the radiographic properties of the materials, and across 5 slices of a large window of data containing a single sphere was calculated. For each volume element (voxel) within the window that exceeded the threshold, the voxel's value was used as a multiplier on the voxel's 3D position; the averaged value was taken as the center of the sphere. Algebraically, let $b=[b_x, b_y, b_z]^T$ be a point in the CT volume of interest in which the sphere appears. Further let I(b) be the thresholded image intensity at b, that is, $I(b)>0$ if and only if the original CT intensity at b exceeds the radiographic threshold. Then, summing over a volume that contains all of the marker voxels, the bead center p is $$\vec{p} = \frac{\Sigma_i\Sigma_j\Sigma_k [b_i\ b_j\ b_k]^T I(b_i, b_j, b_k)}{(\Sigma_i\Sigma_j\Sigma_k I(b_i, b_j, b_k))}$$

$$= \frac{\Sigma_i\Sigma_j\Sigma_k\ \vec{b}_{ijk} I(\vec{b}_{ijk})}{(\Sigma_i \Sigma_j \Sigma_k I(\vec{b}_{ijk}))}$$

The third measurement was with a mechanical pointing arm (FARO Technologies model B08-02). The arm was calibrated at the factory with a measured pointer-tip location lying within ±0.3 mm of its Cartesian location at least 95% of the time. For these studies, a custom probe tip was fabricated and calibrated against a factory probe by using an optical comparator. An additional 0.4 mm was subtracted from the probe length to compensate for the radius of an RSA marker, that is, after the compensation the measured tip location was intended to measure the center of a marker. In four orientation trials, the phantoms were fixed within the pointer workspace and each marker was touched in sequence.

Experimental Results

To establish the accuracy of a measurement, it must be compared to a "ground truth". In this study the RSA measurements were taken as true, and the CT and pointer data were referred to the RSA data.

Accuracy was measured by the root-mean-square (RMS) of the norm of the residuals of the registration. Using the notation of Equation 1, let $p_i$ be the location of a source marker and let $x_i$ be the location of a reference marker. The residual error $r_i$ of transforming $p_i$ under the registration is $$\vec{r}_i = \vec{x}_i - R\vec{p}_i - \vec{q}$$

and the RMS error $E_j$ of a given registration is $$E_j = \sqrt{\frac{\sum_{i=1}^{n} \|\vec{r}_i\|^2}{n}}$$

If k registrations of different data sets are performed, the overall RMS error E is the RMS error of all of the residuals, or equivalently $$E = \sqrt{\frac{\sum_{j=1}^{k} E_j^2}{k}}$$

The RMS error of registering a modality to itself is a measurement of the repeatability of the modality, and the RMS error of registering one modality to another is a measurement of the relative accuracy. Since RSA is taken as the ground truth, registering to RSA data is taken as a measurement of absolute accuracy.

The first step was to establish the utility of the RSA data. The seven RSA sets of femoral data were registered to each other to produce 42 registrations, as were the seven sets of tibial data; the residual errors of all 84 registrations were then calculated. The overall RMS registration error was 0.043 mm, which indicates that in seven distinct orientations the markers behaved as a rigid body in each phantom. The RMS error from each registration, for each phantom, is given in the Appendix.

The next step was to verify the repeatability of identifying the marker locations from the CT images and from the pointer data. For three sets of CT-based marker locations, registering CT set to all other CT sets for each phantom and calculating the residuals produced an overall RMS error of 0.120 mm. For four sets of locations from pointer data, the overall RMS error was 0.158 mm. The CT processing was surprisingly repeatable, and the pointer processing was well within the expected limits of the device.

The RSA data were thus taken as the ground truth, and the other modalities registered to RSA. The CT fiducial centers were registered to RSA in all 42 ways (21 for each of 2 objects), with an overall RMS error of 0.152 mm. The pointer data were registered to RSA in all 52 ways (28 for each 2 objects), with an overall RMS error of 0.220 mm.

Finally the CT data and pointer data were registered, which is the interesting case for surgical application. The 24 tests had an overall RMS error of 0.251 mm, which is only ¼ of the slice width of the CT scan. Table 1 summarizes the results, with the diagonal elements representing the repeatability tests and the other elements representing the cross-registration results.

TABLE 1

| Cross-Registration RMS Error of Sensing Modalities, in mm | | | |
| --- | --- | --- | --- |
| Modality | RSA | CT | Pointer |
| RSA | 0.043 | 0.152 | 0.220 |
| CT | 0.152 | 0.120 | 0.251 |
| Pointer | 0.220 | 0.251 | 0.158 |

It will be appreciated by those skilled in the art that a method has been described for registering CT images of phantoms that contain fiducial markers to data gathered from a pointing device. While particular emphasis has been placed on the use of this method in computer-aided or robotic surgery, it will be appreciated that the method will be used in many other machining applications and even in such applications as forensic archeology and pathology.

Figure 5:
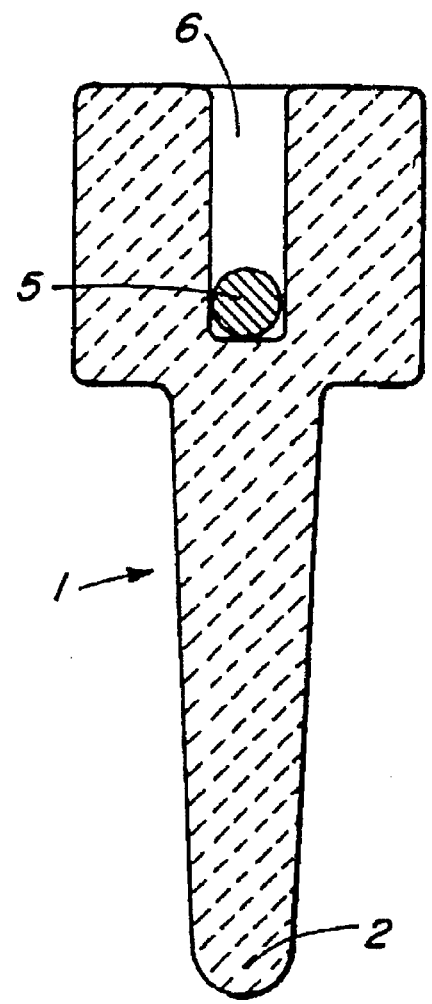
FIG. 5 is a sketch of one embodiment of a ceramic surgical pin of the present invention.

As noted hereinabove, the fiducial marker for use in surgical applications should be biocompatible as it may be left in the body for a long period of time. The 0.80 mm diameter spherical marker is preferably fabricated from a biocompatible metal or metal alloy such as tantalum, gold, stainless steel, Vitallium® or other cobalt-chrome alloy. However, because it is of such small diameter and there is a need to be able to locate it months or even years after insertion into the body, it is preferable that the marker is contained within a biocompatible radio luscent holder which is of sufficient size that it can be manually located through the skin or other overlying tissue. One embodiment of a holder for the spherical marker is illustrated in FIG. 5. In FIG. 5 an elongated radio luscent ceramic pin 1 approximately 9.0 mm long having a tapered tail portion 2, approximately 1–1.5 mm in diameter and about 6 mm long, and a head portion 3, approximately 3.5 mm diameter and about 3.0 mm long is provided. Head 3 is provided with an axial bore 4, about 0.08 mm in diameter and about 2.6 mm deep, into which a metallic marker sphere 5, about 0.8 mm diameter, is inserted and secured either by a friction fit or with the use of a biocompatible radio luscent adhesive such as Pro-bond Cement (Dentspy). Preferably, but not essentially, sphere 5 is a tantalum sphere. The ceramic material employed for pin 1 is preferably an alumina ceramic which is radio luscent, biocompatible and has relatively high physical strength. Zirconia ceramics are generally unsatisfactory as they are generally radio-opaque and it has been found that hydroxyapatite ceramics are generally too fragile. Preferably, the head end 6 of bore 4 is open to facilitate insertion of a pointer (not shown) equipped with a force sensor as described above. In the event that the pin 1 is overgrown with tissue, after location thereof through the tissue a surgical incision may be made to expose the pin 1 and marker sphere 5.

It will be appreciated that the RSA and mechanical arm techniques for gathering data, represent only two of numerous techniques which may be employed. For example, ultrasonic positioning sensors, 3D optical tracking devices, laser range sensors, stereoscopic cameras, fluorscopic x-ray detectors and 3D magnetic position sensors may also be used.

I claim:

1. A method for deriving high accuracy correlation between data obtained by a computed tomography (CT) scan, in which an object is scanned in a plurality of CT slices, and data relating to said object obtained from other sources, comprising:

providing in said object at least one radio-opaque marker having a diameter less than one slice width of said CT scan;

detecting said radio-opaque marker in at least two said slices; and determining a three dimensional position of said marker therefrom for comparison with said from other sources.

2. A method as claimed in claim 1 wherein said radio-opaque marker is a biocompatible metallic marker for implantation into a bone.

3. A method as claimed in claim 1 including the step of detecting a plurality of said markers with a sensor operatively coupled to a calibrating device.

4. A method as claimed in claim 1 wherein said other data is derived from at least one of (a) Roentgen stereogrammetric analysis (b) a mechanical pointing arm, (c) ultrasonic position sensor, (d) 3D optical tracking device (3) laser range sensor (f) stereoscopic camera (g) fluorscopic x-ray detector and (h) 3D magnetic position sensor.

5. A method as claimed in claim 3 wherein said calibrating device comprises an optical comparitor.

6. A method as claimed in claim 2 including surgically implanting said radio-opaque marker in a radio luscent biocompatible holder therefor, into a patient.

7. A marker for use in computed tomography (CT) scanning, comprising:

a radio-opaque marker elment;

a radio luscent holder adapted to receive said marker element; and means to secure said marker in said holder;

wherein said marker element has a diameter less than one CT scan slice width.

8. A marker as claimed in claim 7 wherein said radio luscent holder comprises a ceramic holder.

9. A marker as claimed in claim 8 wherein said radio luscent holder is an alumina holder.

10. A marker as claimed in claim 7 wherein said radio-opaque marker element is a sphere.

11. A marker as claimed in claim 10 wherein said sphere is a biocompatible metal.

12. A marker as claimed in claim 11 wherein said biocompatible metal is selected from the group consisting of tantalum, stainless steel, titanium alloys, and chrome-cobalt alloys.

13. A marker as claimed in claim 7 wherein said means to secure said marker element in said holder comprises a biocompatible, radio luscent adhesive material.

14. A marker as claimed in claim 7 wherein said holder comprises an elongated ceramic pin member having a longitudinal axial bore at one end thereof adapted to receive said marker element therein.

15. A system for deriving high accuracy correlation between data obtained by a CT scan, and data obtained from other sources, comprising:

(a) means for CT scanning in a plurality of slices of selected bandwith;

(b) radio opaque marker means having a diameter of less than said selected bandwidth;

(c) means for detecting said radio opaque marker in at least two said slices; and (d) means for deriving said data obtained from other sources.

16. A system as claimed in claim 15 wherein said means for deriving said data obtained from other sources is selected from (a) Roentgen stereogrammatic analysis means (b) a mechanical pointing arm, (c) ultrasonic position sensor, (d) 3D optical tracking device, (e) laser range sensor (f) stereoscopic camera (g) fluorscopic x-ray detector and (h) 3D magnetic position sensor.

17. A system as claimed in claim 16 wherein said mechanical arm includes sensor means for detecting a plurality of said marker means, operatively coupled to a calibrating device.

18. A system as claimed in claim 17 wherein said sensor means comprises means to touch said marker means.

19. A system as claimed in claim 18 wherein said calibrating device comprises optical calibration means.

\* \* \* \* \*